(12) United States Patent
Grey et al.

(10) Patent No.: US 8,512,234 B2
(45) Date of Patent: Aug. 20, 2013

(54) LARYNGOSCOPE ASSEMBLY WITH ENHANCED VIEWING CAPABILITY

(75) Inventors: David Grey, Ramat Efal (IL); Eugeny Pecherer, Netanya (IL)

(73) Assignee: Truphatek International Ltd., Netanya (IL)

( * ) Notice: Subject to any disclaimer, the term of this patent is extended or adjusted under 35 U.S.C. 154(b) by 0 days.

(21) Appl. No.: 13/439,222

(22) Filed: Apr. 4, 2012

(65) Prior Publication Data

US 2012/0259176 A1    Oct. 11, 2012

(30) Foreign Application Priority Data

Apr. 7, 2011 (IL) .......................................... 212204

(51) Int. Cl.
*A61B 1/267*     (2006.01)
(52) U.S. Cl.
USPC .......................................... 600/193; 600/185
(58) Field of Classification Search
USPC .................................................. 600/184–200
See application file for complete search history.

(56) References Cited

U.S. PATENT DOCUMENTS

| | | |
|---|---|---|
| 330,139 A | 11/1885 | Meyer |
| 2,433,705 A | 12/1947 | Palmeter |
| 3,426,749 A | 2/1969 | Jephcott |
| 3,598,113 A | 8/1971 | Moore et al. |
| 3,638,644 A | 2/1972 | Reick |
| 3,766,909 A | 10/1973 | Ozbey |
| 3,826,248 A | 7/1974 | Gobels |
| 3,856,001 A | 12/1974 | Phillips |
| 3,874,371 A | 4/1975 | Stader et al. |
| 3,900,021 A | 8/1975 | Makepeace et al. |
| 4,037,588 A | 7/1977 | Heckele |
| 4,086,919 A | 5/1978 | Bullard |
| 4,273,112 A | 6/1981 | Heine et al. |
| 4,306,547 A | 12/1981 | Lowell |
| 4,406,280 A | 9/1983 | Upsher |

(Continued)

FOREIGN PATENT DOCUMENTS

| | | |
|---|---|---|
| DE | 26 21 232 | 11/1977 |
| DE | 85 26 662 | 10/1985 |

(Continued)

OTHER PUBLICATIONS

Search Report for PCT/IL2012/000151 mailed Aug. 15, 2012.

(Continued)

*Primary Examiner* — Ellen C Hammond
*Assistant Examiner* — Jacqueline Johanas
(74) *Attorney, Agent, or Firm* — Novick, Kim & Lee, PLLC; Harold L. Novick

(57) ABSTRACT

A laryngoscope assembly with enhanced viewing capability including a laryngoscope handle having a permanently mounted laryngoscope optical system. The laryngoscope optical system has a view tube with a leading aperture lens for affording a field of view along a deflected line of sight viewing in an operative intubation position. The laryngoscope handle includes a laryngoscope optical system securing arrangement for mechanically securing the laryngoscope optical system in the operative intubation position. The laryngoscope assembly also includes an interchangeable laryngoscope blade including a trailing view tube sleeve for slidably mounting on the view tube and a leading spatula wherein the view tube sleeve has a leading transparent window for covering the aperture lens. The laryngoscope assembly further includes a blade securing arrangement for mechanically securing the laryngoscope blade on the laryngoscope handle in the operative intubation position.

3 Claims, 6 Drawing Sheets

(56) References Cited

U.S. PATENT DOCUMENTS

| | | |
|---|---|---|
| 4,437,458 A | 3/1984 | Upsher |
| 4,527,553 A | 7/1985 | Upsher |
| 4,556,052 A | 12/1985 | Muller |
| 4,557,256 A | 12/1985 | Bauman |
| 4,565,187 A | 1/1986 | Soloway |
| 4,570,614 A | 2/1986 | Bauman |
| 4,579,108 A | 4/1986 | Bauman |
| 4,583,527 A | 4/1986 | Musicant et al. |
| 4,596,239 A | 6/1986 | Bauman |
| 4,679,547 A | 7/1987 | Bauman |
| 4,878,486 A | 11/1989 | Slater |
| 4,884,558 A | 12/1989 | Gorski et al. |
| 4,901,708 A | 2/1990 | Lee |
| 4,924,855 A | 5/1990 | Salerno et al. |
| 4,930,495 A | 6/1990 | Upsher |
| 4,958,624 A | 9/1990 | Stone et al. |
| 4,972,825 A | 11/1990 | Vescovo, Jr. |
| 5,060,633 A | 10/1991 | Gibson |
| 5,065,738 A | 11/1991 | Van Dam |
| 5,178,131 A | 1/1993 | Upsher |
| 5,263,472 A | 11/1993 | Ough |
| 5,355,870 A | 10/1994 | Lacy |
| 5,363,838 A | 11/1994 | George |
| 5,501,651 A | 3/1996 | Bauman |
| 5,529,570 A | 6/1996 | Storz |
| 5,609,561 A | 3/1997 | Uehara et al. |
| 5,643,221 A | 7/1997 | Bullard |
| 5,651,760 A | 7/1997 | Upsher |
| 5,695,454 A * | 12/1997 | Mourkidou ............... 600/186 |
| 5,702,351 A | 12/1997 | Bar-Or et al. |
| 5,776,053 A | 7/1998 | Dragisic et al. |
| 5,827,178 A | 10/1998 | Berall |
| 5,836,867 A | 11/1998 | Speier et al. |
| 5,842,973 A | 12/1998 | Bullard |
| 5,846,186 A | 12/1998 | Upsher |
| 5,873,818 A | 2/1999 | Rothfels |
| 5,879,304 A | 3/1999 | Shuchman et al. |
| 5,888,195 A | 3/1999 | Schneider |
| 5,951,461 A | 9/1999 | Nyo et al. |
| 5,973,728 A | 10/1999 | Levitan |
| 6,013,026 A | 1/2000 | Krauter et al. |
| 6,036,639 A | 3/2000 | Allred, III et al. |
| 6,083,151 A * | 7/2000 | Renner et al. ............. 600/114 |
| 6,123,666 A | 9/2000 | Wrenn et al. |
| 6,139,491 A | 10/2000 | Heine et al. |
| 6,213,937 B1 | 4/2001 | Vivenzio |
| 6,346,073 B1 | 2/2002 | Thompson |
| 6,350,235 B1 | 2/2002 | Cohen et al. |
| 6,354,993 B1 | 3/2002 | Kaplan et al. |
| RE37,861 E | 9/2002 | Schneider |
| 6,444,358 B1 | 9/2002 | Allred, III et al. |
| 6,508,759 B1 | 1/2003 | Taylor et al. |
| 6,652,453 B2 | 11/2003 | Smith et al. |
| 6,655,377 B2 | 12/2003 | Pacey |
| 6,676,598 B2 | 1/2004 | Rudischhauser et al. |
| 6,719,688 B2 | 4/2004 | Pecherer et al. |
| 6,805,665 B1 | 10/2004 | Tatsuno et al. |
| 6,840,903 B2 | 1/2005 | Mazzei et al. |
| 6,964,637 B2 | 11/2005 | Dalle et al. |
| 7,044,910 B2 | 5/2006 | Cartledge et al. |
| 7,128,710 B1 | 10/2006 | Cranton et al. |
| 7,214,184 B2 | 5/2007 | McMorrow |
| 7,338,440 B1 | 3/2008 | Smith |
| 7,500,948 B2 | 3/2009 | Cantrell |
| 7,608,040 B1 | 10/2009 | Dunst |
| 7,736,304 B2 | 6/2010 | Pecherer |
| 7,771,350 B2 | 8/2010 | Geist et al. |
| 7,802,909 B2 | 9/2010 | Baker |
| 7,909,759 B2 | 3/2011 | Pecherer |
| 7,946,981 B1 | 5/2011 | Cubb |
| 2001/0014768 A1 | 8/2001 | Kaplan et al. |
| 2002/0082477 A1 | 6/2002 | Kim |
| 2002/0082478 A1 | 6/2002 | McGrath |
| 2002/0087050 A1 * | 7/2002 | Rudischhauser et al. ..... 600/199 |
| 2003/0092967 A1 | 5/2003 | Fourie et al. |
| 2003/0195390 A1 | 10/2003 | Graumann |
| 2004/0034281 A1 | 2/2004 | Cartledge et al. |
| 2004/0122292 A1 | 6/2004 | Dey et al. |
| 2004/0127770 A1 | 7/2004 | McGrath |
| 2004/0210108 A1 | 10/2004 | Shimizu et al. |
| 2004/0215062 A1 | 10/2004 | Dalle et al. |
| 2004/0220454 A1 * | 11/2004 | Dalle et al. .................. 600/186 |
| 2005/0090712 A1 | 4/2005 | Cubb |
| 2006/0276693 A1 * | 12/2006 | Pacey ........................... 600/188 |
| 2007/0093693 A1 | 4/2007 | Geist et al. |
| 2007/0167686 A1 | 7/2007 | McGrath |
| 2008/0004498 A1 | 1/2008 | Pecherer |
| 2008/0045801 A1 * | 2/2008 | Shalman et al. .............. 600/193 |
| 2009/0065007 A1 | 3/2009 | Wilkinson et al. |
| 2009/0209816 A1 | 8/2009 | Nielsen et al. |
| 2009/0299146 A1 | 12/2009 | McGrath |
| 2010/0022843 A1 * | 1/2010 | Pecherer et al. ............. 600/197 |
| 2010/0191061 A1 * | 7/2010 | Simons ........................ 600/186 |
| 2010/0261967 A1 | 10/2010 | Pacey et al. |
| 2010/0261968 A1 | 10/2010 | Nearman et al. |
| 2011/0060190 A1 | 3/2011 | Pecherer |
| 2011/0319718 A1 * | 12/2011 | Hakanen et al. ............. 600/193 |
| 2012/0330103 A1 * | 12/2012 | Tenger et al. ................ 600/188 |

FOREIGN PATENT DOCUMENTS

| | | |
|---|---|---|
| DE | 202 18 560 | 5/2003 |
| EP | 0 184 588 | 6/1986 |
| EP | 0 653 180 | 5/1995 |
| GB | 685741 | 1/1953 |
| GB | 806467 | 12/1958 |
| GB | 2437435 | 10/2007 |
| WO | WO 2004/096032 | 11/2004 |
| WO | WO 2006/056976 | 6/2006 |
| WO | WO 2006/131770 | 12/2006 |
| WO | WO 2007/066134 | 6/2007 |
| WO | WO 2009/019703 | 2/2009 |

OTHER PUBLICATIONS

Medizintechnik KaWe Germany, Laryngoskope, Megalight F.O. (Publication date unknown).

Rüsch Inc. "Care and Maintenance instructions for Rüsch Laryngoscope Handles and Blades," 2001.

Machine translation of DE 26 21 232.

Machine translation of DE 85 26 662.

Machine translation of DE 202 18 560.

\* cited by examiner

LARYNGOSCOPE ASSEMBLY WITH ENHANCED VIEWING CAPABILITY

CROSS-REFERENCE TO RELATED APPLICATIONS

This application claims priority of Israel Patent Application No. 212204 filed Apr. 7, 2011, the disclosure of which is incorporated by reference herein in its entirety.

FIELD OF THE INVENTION

The invention relates to laryngoscope apparatus with enhanced viewing capability.

BACKGROUND OF THE INVENTION

Commonly owned PCT International Patent Application No. PCT/IL2008/001093 entitled Laryngoscope Apparatus with Enhanced Viewing Capability published under PCT International Publication No. WO 2009/019703 illustrates and describes a laryngoscope assembly including a laryngoscope optical system for affording a field of view along a deflected line of sight for reducing patient manipulation and/or the degree of force required to achieve a good glottic view. The laryngoscope apparatus can be implemented as a laryngoscope blade with either an integral laryngoscope optical system or intended for use with a discrete optical view tube. Such laryngoscope blades can be either permanently mounted on a laryngoscope handle and pivotal between an inoperative storage position and an operative intubation position in a penknife-like manner or detachably mounted on a laryngoscope handle. Such laryngoscope blades preferably include an illumination arrangement for providing illumination light for assisting intubation and a defogging arrangement for defogging their forwardmost concave inclined prism surface. Laryngoscope optical systems for providing enhanced viewing capability during intubations are relatively expensive therefore militating against their use as disposable single use items.

SUMMARY OF THE INVENTION

The present invention is directed towards laryngoscope assemblies including (a) a laryngoscope handle including i) a permanently mounted laryngoscope optical system having a view tube with a leading aperture lens for enhanced viewing capability in an operative intubation position and ii) a laryngoscope optical system securing arrangement for mechanically securely the laryngoscope optical system in the operative intubation position, (b) an interchangeable laryngoscope blade including a trailing view tube sleeve for removable sliding mounting on the view tube and a leading spatula wherein the view tube sleeve has a leading transparent window for covering the aperture lens, and (c) a blade securing arrangement for mechanically securing the laryngoscope blade on the laryngoscope handle in the operative intubation position.

The laryngoscope blades of the present invention necessarily include a leading transparent window for covering an aperture lens. Suitable medical grade transparent materials include inter alia rigid plastic materials such as polycarbonate, and the like. The view tube sleeve and the leading spatula may or may not be formed from the same material as the leading transparent window. The laryngoscope blades can be designed as disposable single use items or intended for sterilization for multiple use. The present invention affords a more convenient arrangement for providing laryngoscope apparatus with enhanced viewing capabilities than the hitherto described arrangements by way of precluding the need sterilizing a view tube between intubations.

The permanently mounted laryngoscope optical systems are preferably pivotal on a laryngoscope handle in a penknife-like manner between an inoperative storage position and an operative intubation position. Alternatively, laryngoscope optical systems can be permanently mounted in a transverse position on a laryngoscope handle in an operative intubation position. Suitable laryngoscope optical systems include inter alia U.S. Pat. No. 5,873,818's optical arrangement, aforesaid WO 2009/019703's laryngoscope optical system, and the like. The laryngoscope assemblies preferably include a defogging arrangement for defogging a leading transparent window covering an aperture lens.

The laryngoscope assemblies preferably include an illumination arrangement for providing illumination at its operative intubation position. One illumination arrangement includes inter alia a laryngoscope handle having a power supply and a view tube having an illumination source towards its leading aperture lens. Another illumination arrangement includes inter alia a laryngoscope handle having both a power pack and an illumination source and a view tube having a light transmission arrangement for conveying light from the illumination source to its leading aperture lens. Alternatively, a laryngoscope blade can be employed instead of a view tube for illumination purposes.

BRIEF DESCRIPTION OF DRAWINGS

In order to understand the invention and to see how it can be carried out in practice, a preferred embodiment will now be described, by way of a non-limiting example only, with reference to the accompanying drawings in which similar parts are likewise numbered, and in which.

DETAILED DESCRIPTION OF A PREFERRED EMBODIMENT OF THE INVENTION

Figure 1:
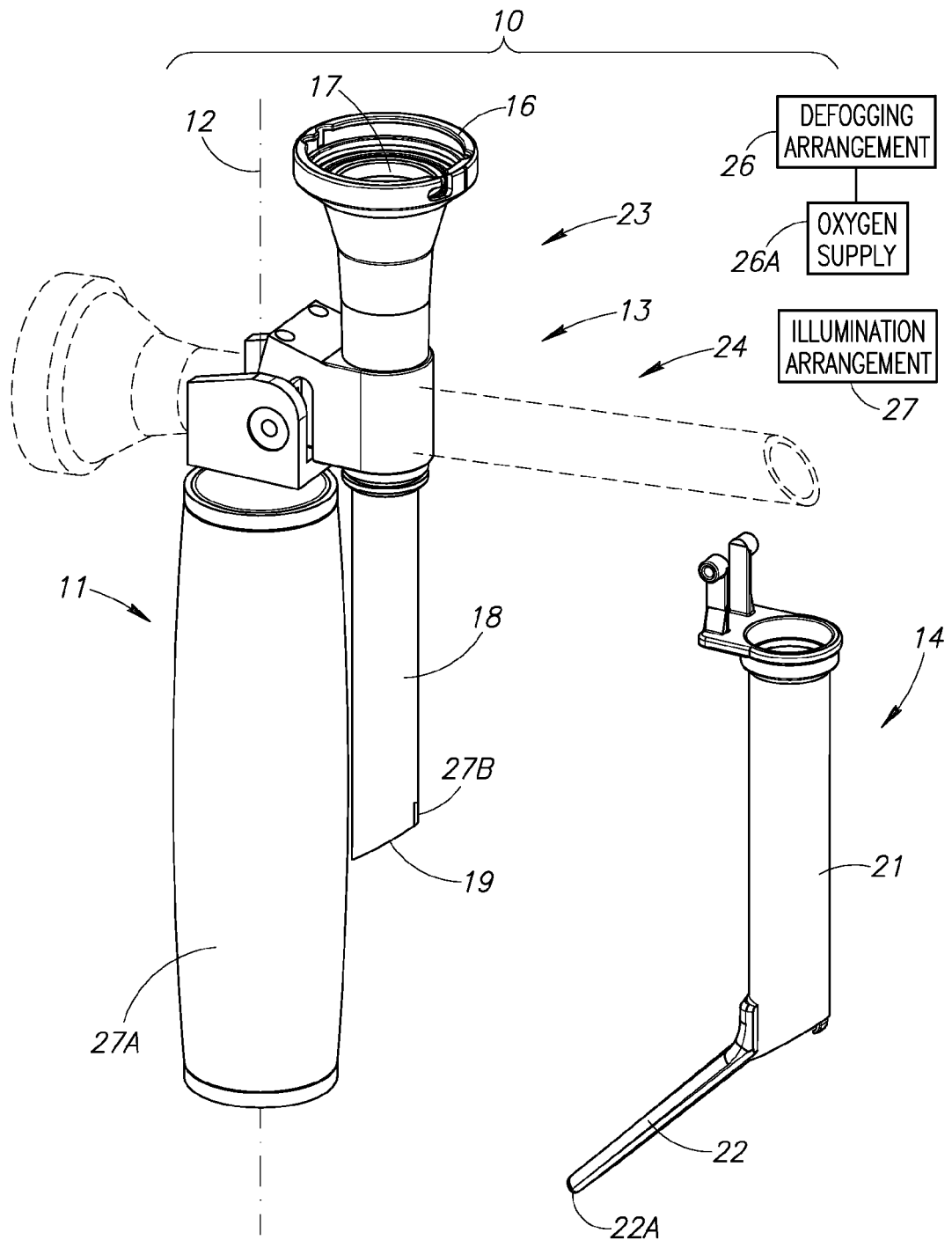
FIG. 1 is a perspective view of a dissembled laryngoscope assembly including a laryngoscope handle with a permanently mounted laryngoscope optical system and an interchangeable laryngoscope blade.
Figure 3:
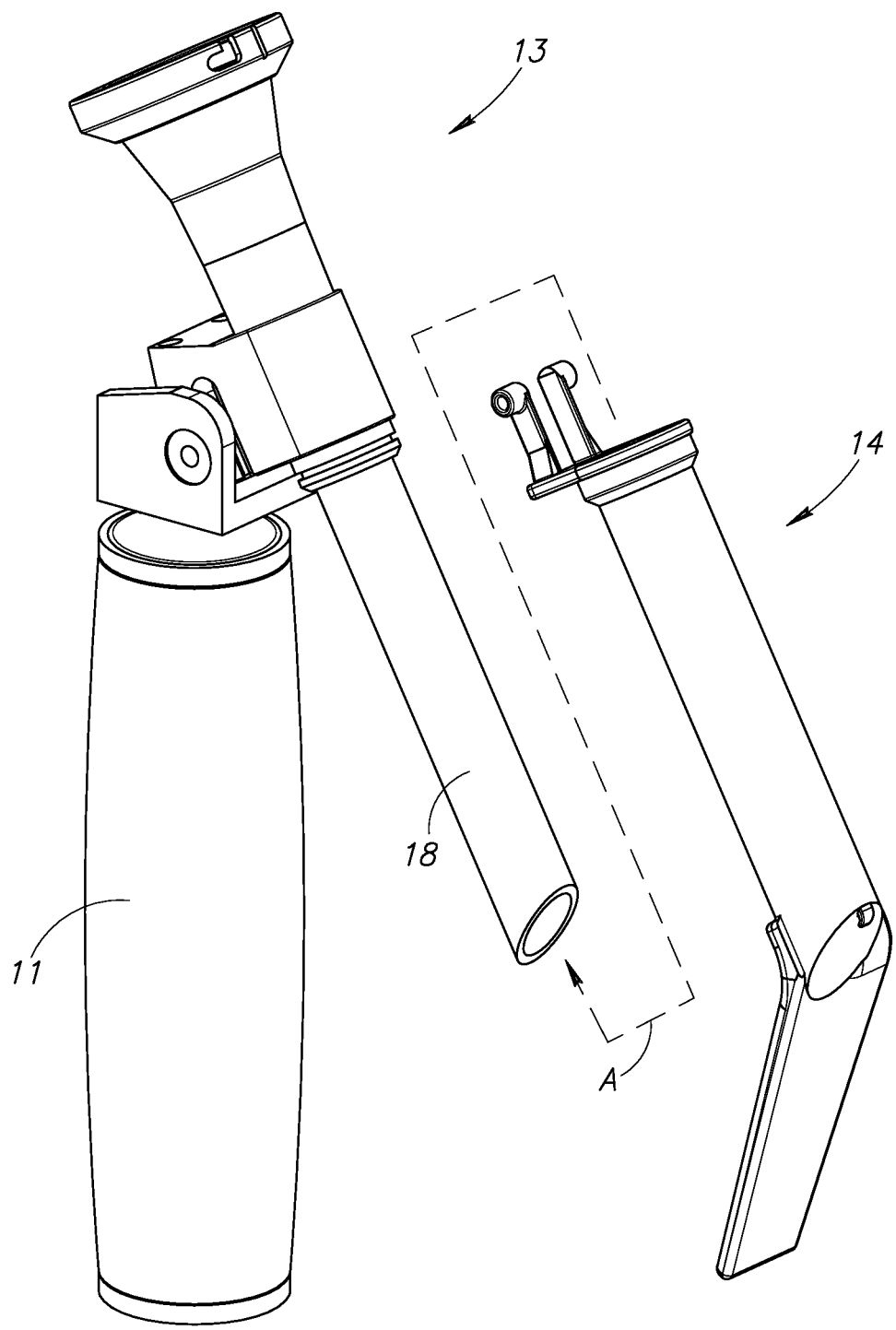
FIG. 3 is a perspective view showing the laryngoscope handle and its laryngoscope optical system in a blade mounting position and the sliding mounting of the laryngoscope blade on the laryngoscope handle.

FIG. 1 shows a laryngoscope assembly 10 including a laryngoscope handle 11 having a longitudinal axis 12 and a permanently mounted laryngoscope optical system 13, and an interchangeable laryngoscope blade 14. The laryngoscope optical system 13 is pivotal between an inoperative storage position shown in solid lines and an operative intubation position shown in dashed lines. The laryngoscope optical system 13 includes an eyepiece 16 having an eye lens 17 and a view tube 18 with a leading forwardly inclined aperture lens 19 for affording a field of view along a deflected line of sight viewing in an operative intubation position with the view tube 18 transversely directed to the longitudinal axis 12. The laryngoscope blade 14 includes a trailing view tube sleeve 21 and a leading spatula 22 having a spatula tip 22A. The laryngoscope handle 11 includes a laryngoscope optical system securing arrangement 23 for mechanically securing the laryngoscope optical system 13 in the operative intubation position. Suitable laryngoscope optical system securing arrangements 23 include inter alia spring mounted ball bearing arrangements, for example, as illustrated and described in commonly owned WO 03/043484 FIG. 3.

The laryngoscope assembly 10 includes a blade securing arrangement 24 for mechanically securing the laryngoscope blade 14 on the laryngoscope handle 11 in the operative intubation position. The laryngoscope assembly 10 includes a defogging arrangement 26 including an external oxygen supply 26A for providing a clear view through the laryngoscope optical system 13 in the operative intubation position. The laryngoscope assembly 10 includes an illumination arrangement 27 for providing illumination in the operative intubation position. The laryngoscope handle 11 includes a power supply 27A and the view tube 18 includes an illumination source 27B adjacent its leading aperture lens 19. The illumination source 27B is in electrical connection with the power supply 27A in the operative intubation position.

Figure 2:
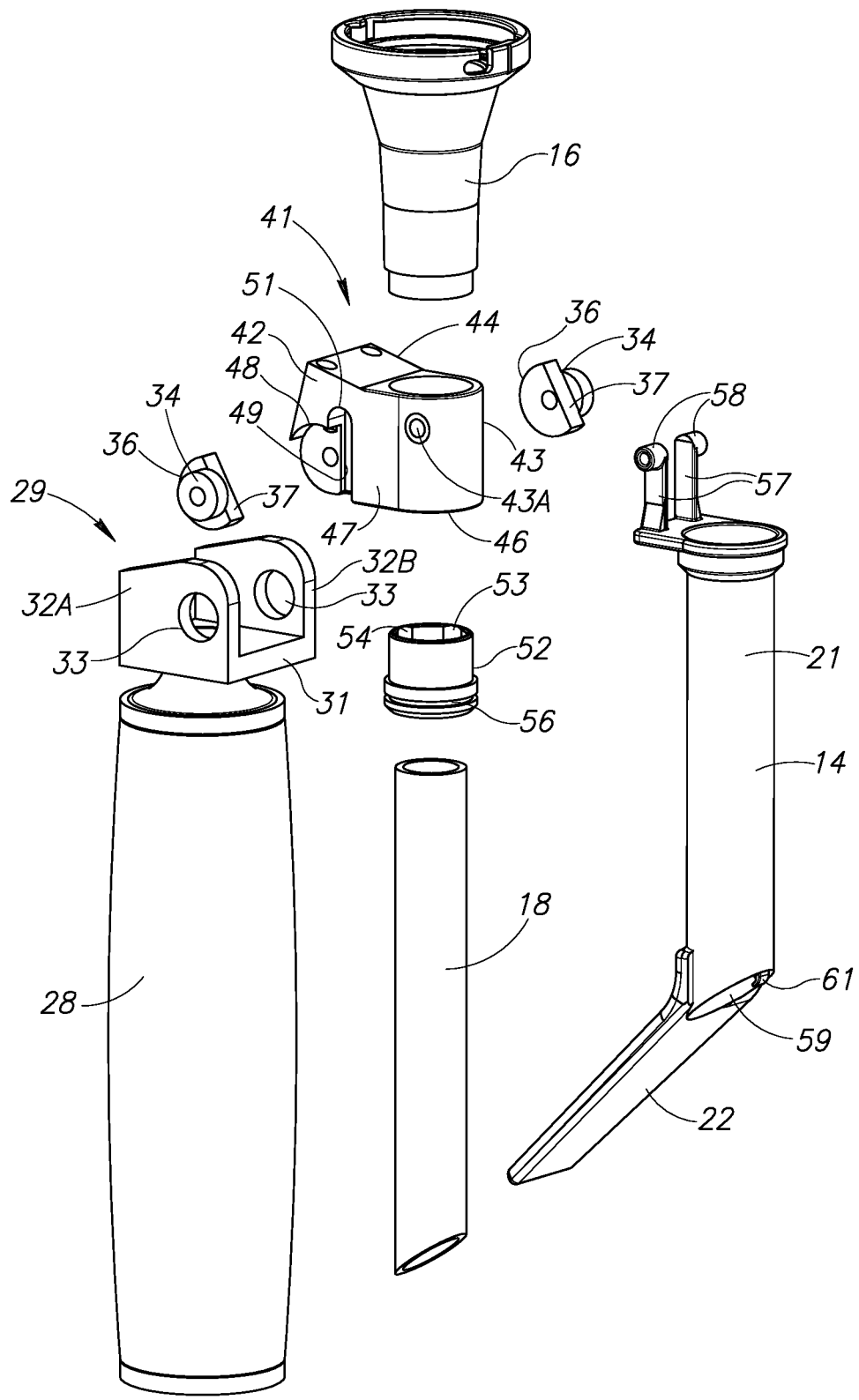
FIG. 2 is an exploded view of FIG. 1's laryngoscope assembly.

FIG. 2 shows the laryngoscope handle 11 includes a handle 28 with a head 29 including a base 31 and opposite and parallel upright left and right walls 32A and 32B. The side walls 32 include a leading pair of opposite circular apertures 33. The apertures 33 are fitted with a pair permanent immovable supports 34 each having a rounded peripheral surface 36 and an inner flat support surface 37 subtending an included 30° angle with respect to the longitudinal axis 12.

The laryngoscope handle 11 includes a laryngoscope optical system support 41 including a base portion 42 for pivotal mounting on the supports 34 and an upper tubular portion 43 having an oxygen port 43A for snap fit sealed connection to the oxygen supply 26A. The support 41 has a trailing side 44 and a leading side 46. The eyepiece 16 is sealingly mounted on the trailing side 44. The view tube 18 is mounted in the leading side 46. The base portion 42 has a pair of opposite and parallel left and right side surfaces 47 each formed with a trailing rounded surface 48 for reciprocal movement along the rounded peripheral surfaces 36 and a track 49 extending lengthwise from the trailing side 44 to the leading side 46. The tracks 49 each have a closed track end 51 at the trailing side 44. The flat support surfaces 37 and the tracks 49 form a pair of grooves in a blade insertion position of the laryngoscope optical system 13 relative to the laryngoscope handle 11 for enabling sliding insertion of the laryngoscope blade 14 on the view tube 18.

A washer 52 is interposed between the tubular portion 43 and the view tube 18. The washer 52 has an internal surface 53 formed with a series of longitudinal directed channels 54 for enabling a flow of defogging oxygen from the oxygen port 43A along the tubular separation between the view tube 18 and the view tube sleeve 21. The washer 52 is provided with an O ring 56 for ensuring sealing between the upper tubular portion 43 and the view tube sleeve 21.

The view tube sleeve 21 includes a pair of left and right rearward directed legs 57 each with an outward directed protrusion 58. The blade securing arrangement 24 for mechanically securing the laryngoscope blade 14 on the laryngoscope handle 12 are constituted by the supports 34, the base portion 42 and the legs 57 as follows: The legs 57 are intended to be slidingly inserted into the pair of grooves formed between the supports 34 and the base portion 42 in the laryngoscope optical system 13's blade insertion position. Upward movement of the laryngoscope optical system 13 relative to the laryngoscope handle 11 to an intermediate blade securing position between the blade insertion position and the operative intubation position lifts the legs 57 from the support surfaces 37 and locks the protrusions 58 behind the supports 34 thereby preventing sliding removal of the laryngoscope blade 14 from the laryngoscope handle 11.

The laryngoscope blade 14 is made from medical grade transparent rigid plastic material, for example, polycarbonate, and includes a transparent window 59 for covering the leading forwardly inclined aperture lens 19. The laryngoscope blade 14 is formed with an aperture 61 above the window 59 for providing a defogging oxygen flow for defogging the window 59.

FIGS. 3 to 6 show the use of the laryngoscope assembly 10 as follows:

A user disposes the laryngoscope optical system 13 to the blade mounting position for enabling the complete sliding mounting of the laryngoscope blade 14 onto the view tube 18. The user slides the laryngoscope blade 14 onto the view tube 18 as denoted by arrow A until the outward directed protrusions 58 abut against the closed track ends 51 and the view tube sleeve 21's trailing end passes over the O ring 56 (see FIG. 4).

Figure 4:
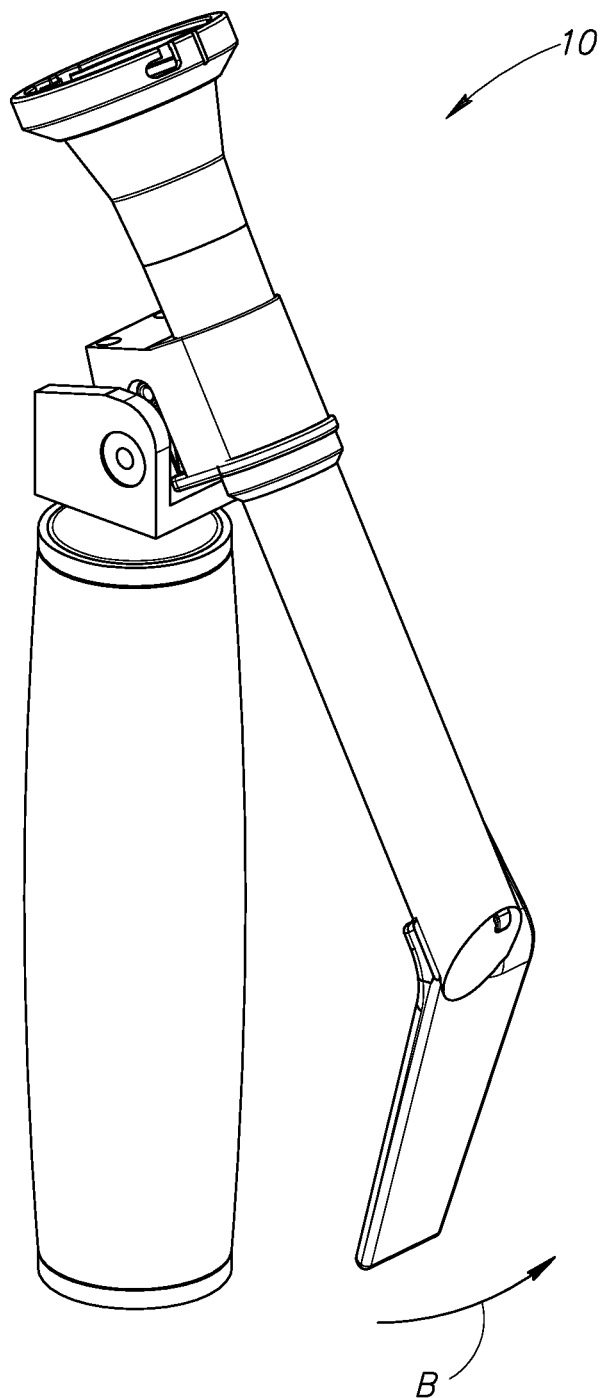
FIG. 4 is a perspective view showing the laryngoscope blade mounted on the laryngoscope handle in FIG. 3's blade mounting position.
Figure 5:
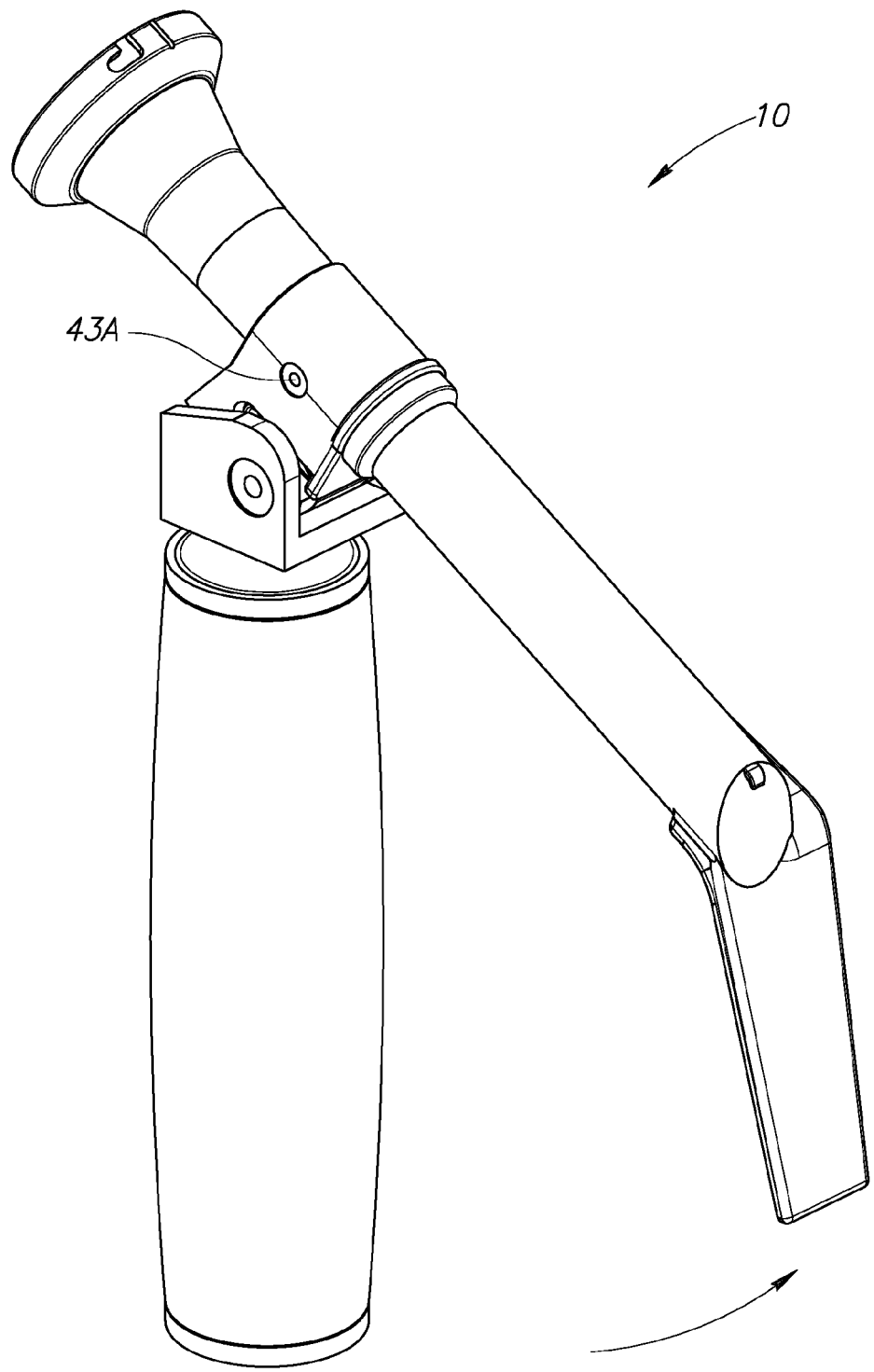
FIG. 5 is a perspective view showing the laryngoscope blade mounted on the laryngoscope handle in a blade securing position.

The user disposes the laryngoscope optical system 13 as denoted by arrow B in FIG. 4 to the blade securing position in which the outward directed protrusions 58 are locked behind the supports 34 thereby preventing removable of the laryngoscope blade 14 from the laryngoscope handle 11 (see FIG. 5). The O ring 56 seals the view tube sleeve 21's trailing end such that the user can attach the oxygen supply 26A to the oxygen port 43A for providing a defogging oxygen flow through the aperture 61 for defogging the window 59.

Figure 6:
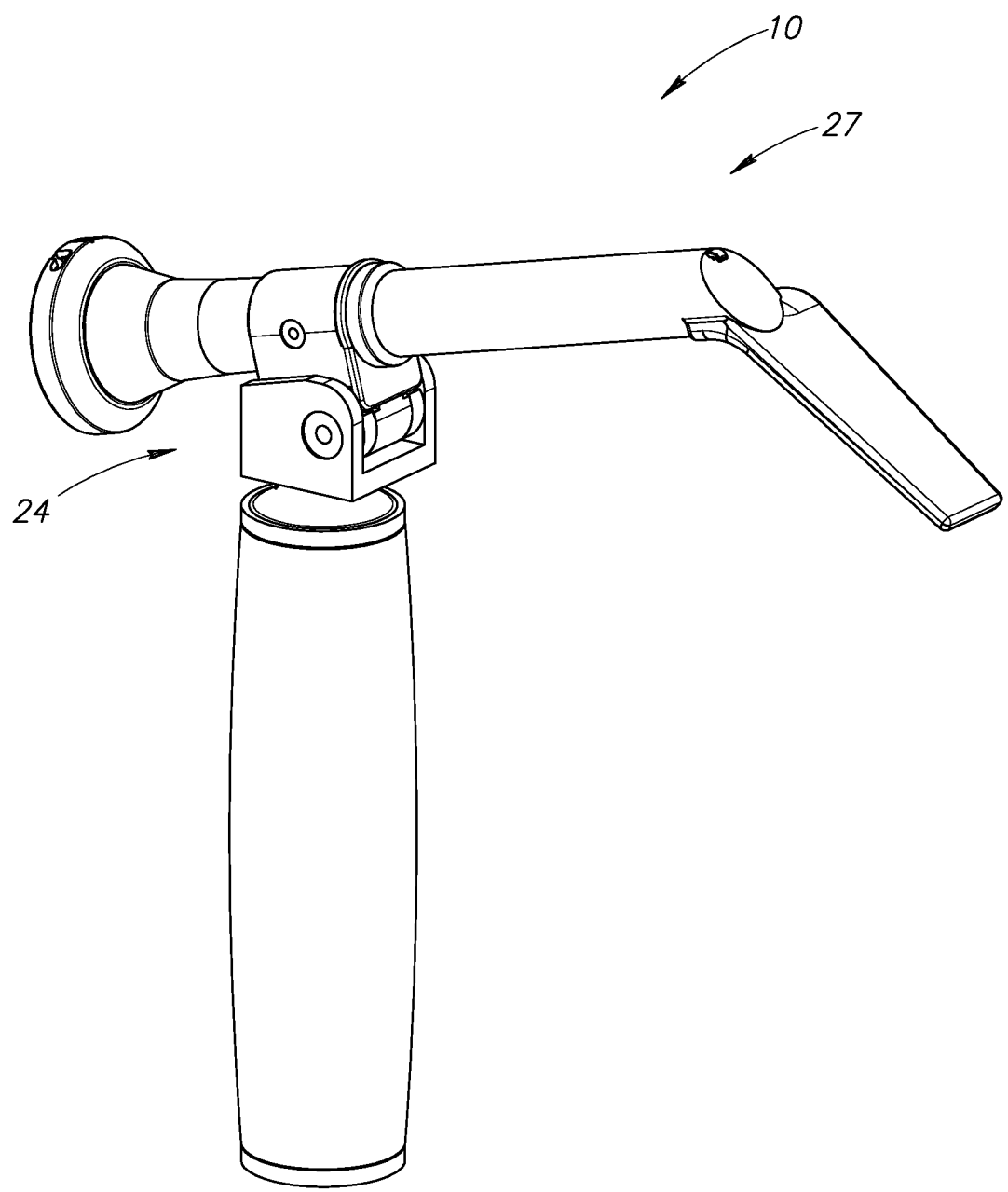
FIG. 6 is a perspective view showing the laryngoscope blade mounted on the laryngoscope handle in an operative intubation position.

The user disposes the laryngoscope optical system 13 as denoted by arrow C in FIG. 5 to the operative intubation position in which the blade securing arrangement 24 mechanically secures the laryngoscope blade 14 on the laryngoscope handle 11 (see FIG. 6). The illumination arrangement 27 is energized in the operative intubation system for providing illumination at a patient's laryngeal region.

While the invention has been described with respect to a limited number of embodiments, it will be appreciated that many variations, modifications, and other applications of the invention can be made within the scope of the appended claims.

The invention claimed is:

1. A laryngoscope assembly with enhanced viewing capability comprising:
   a laryngoscope handle having a longitudinal axis and including
      a permanently mounted laryngoscope optical system having a view tube with a leading aperture lens for affording a field of view along a deflected line of sight viewing in an operative intubation position with said view tube transversely directed to said longitudinal axis, and
      a laryngoscope optical system securing arrangement for mechanically securing said laryngoscope optical system in said operative intubation position;
   an interchangeable laryngoscope blade including a trailing view tube sleeve for slidably mounting on said view tube and a leading spatula wherein said view tube sleeve has a leading transparent window for covering said aperture lens; and a blade securing arrangement for mechanically securing said laryngoscope blade on said laryngoscope handle in said operative intubation position wherein said laryngoscope optical system is pivotal between a blade mounting position in which said laryngoscope blade is slidingly mounted on said view tube and said operative intubation position in which said blade securing arrangement mechanically secures said laryngoscope blade on said laryngoscope handle.

2. The assembly according to claim 1 wherein said interchangeable laryngoscope blade including said leading transparent window is formed from transparent rigid plastic material.

3. The assembly according to claim 1 wherein said laryngoscope blade is sealingly mounted on said laryngoscope handle in said operative intubation position and includes an aperture for providing a defogging flow for defogging said leading transparent window.

* * * * *